United States Patent [19]

Spinner et al.

[11] 4,023,934

[45] May 17, 1977

[54] COLOR INDICATOR APPARATUS FOR PRESENCE OF OXYGEN

[75] Inventors: Ernest Elliott Spinner, Grandview, Mo.; Melvin Wayne Hounsell, Beloit, Wis.

[73] Assignee: Marion Laboratories, Inc., Kansas City, Mo.

[22] Filed: Dec. 22, 1975

[21] Appl. No.: 643,331

[52] U.S. Cl. .............................................. 23/254 R
[51] Int. Cl.² .......................................... G01N 31/22
[58] Field of Search ....... 23/254 R, 232 R, 253 TP; 195/103.5, 127; 128/2 R, 2 W

[56] References Cited

UNITED STATES PATENTS

| | | | |
|---|---|---|---|
| 1,644,014 | 10/1927 | Gordon et al. | 23/254 R |
| 2,487,077 | 11/1949 | Shepherd | 23/232 R |
| 3,022,141 | 2/1962 | Grosskopf | 23/254 R |
| 3,446,596 | 5/1969 | Salivar et al. | 23/253 TP |

OTHER PUBLICATIONS

Hackh's Chemical Dictionary, 4th Edn., McGraw-Hill, pp. 427 & 578.

*Primary Examiner*—Robert M. Reese
*Attorney, Agent, or Firm*—Merriam, Marshall, Shapiro & Klose

[57] ABSTRACT

A color indicator apparatus for determining the presence of oxygen which comprises a container which permits flow of gas thereto, an ampoule in the container, said ampoule containing a redox color indicator liquid, and an absorbent material, for the liquid in the ampoule, in the container. Typically the redox color indicator is methylene blue or resazurin. The apparatus is useful for determining if an anaerobic atmosphere exists around a micro-organism culture.

2 Claims, 3 Drawing Figures

COLOR INDICATOR APPARATUS FOR PRESENCE OF OXYGEN

This invention relates to color indicator apparatus. More particularly, this invention is concerned with color indicator apparatus for determining the presence or absence of oxygen, such as in devices for transporting and storing bacterial cultures of the type which remain viable only when in a gaseous environment or atmosphere low in, or devoid of, oxygen.

Many diseases of man and lower animals are bacterial in origin. The treatment of many bacterial diseases requires that the infecting organism be identified. A drug known to be effective against the infecting organism can then be prescribed.

The identification of an infecting organism is generally by means of a culture obtained from the ill patient or animal. The culture is then transported to a laboratory for determination of the identity of the infecting organism. Such laboratories require highly trained microbiologists and elaborate, expensive equipment. Suitable testing laboratories, accordingly, are not always readily available. It therefore becomes necessary for the patient to visit, or animal be taken to, the laboratory where the culture can be obtained and put immediately into the test procedures or for the culture to be taken at a location remote from the laboratory and then transported to the laboratory for testing.

While the collecting of a culture generally presents no difficulties, the storage and/or transportation of the culture to a testing laboratory under conditions which guarantee the culture will be viable and free of contamination upon arrival presents serious problems. Although contamination from other organisms can generally be avoided by suitable means, the maintenance of a viable culture often requires, in addition to a suitable nutrient medium, the storage and transportation of the culture in a particular gaseous environment which promotes its viability.

Since bacteria of the anaerobic type are known to require an oxygen-deficient or oxygen-free gaseous environment, it is obvious that the transportation of an anaerobic bacteria culture should be effected in an environment having no or little oxygen. Organisms which are obligate anaerobes, such as the bacilli of tetanus, gas-gangrene, botulinus and bacteroides, require the absence of oxygen for proper growth. Although this is generally known by bacteriologists, it is disclosed in Brewer U.S. Pat. No. 3,246,959.

The Brewer U.S. Pat. No. 3,246,959 discloses a gas-producing device for generating an atmosphere conducive for maintaining and increasing the viability of organisms which require a special non-toxic atmosphere. The patent shows the chemical generation of hydrogen, carbon dioxide and acetylene for the purpose of supplying a non-toxic atmosphere to a culture in a container. A platinized wire gauze in the container is heated by electricity for the purpose of completely reacting oxygen in the container.

Anandam U.S. Pat. No. 3,616,263 discloses a culture tube for anaerobic cultures. Oxygen is removed from the tube by use of a divided capsule containing aqueous potassium hydroxide and aqueous pyrogallic acid which when combined form a strong reducing agent for the oxygen.

Although the prior art recognizes the need to maintain various cultures in anaerobic conditions, it has needed a low cost, reliable, disposable color indicator for readily determining if the environment or atmosphere created for storage and/or transport of an anaerobic culture is in fact oxygen-free and if the atmosphere around the culture remains oxygen-free at some future time.

According to the present invention there is provided a color indicator apparatus for determining the presence of oxygen, which comprises a container which permits flow of gas thereto, an ampoule in the container with the ampoule containing a redox color indicator liquid, and an absorbent material in the container. It is intended that when the liquid is released from the ampoule it be taken up by the absorbent material.

Although any suitable form of container can be used, it is advisable that it be in the form of a tube which is open at both ends or in the form of a bag.

When a tube is used it is desirably made of a flexible polymeric material such as polyethylene. By dimensioning the ampoule to fit snugly in the tube, the ampoule may be opened by rupturing or breaking it by means of finger pressure applied to the external surface of the tube adjacent the ampoule. The liquid redox color indicator so released from the ampoule may then be caused to flow onto an absorbent fibrous plug also fit snugly in the tube. The liquid is absorbed in this way and held in place so as to provide a relatively easily seen mass which can be observed through the transparent wall of the tube. By making the absorbent plug of a white fibrous material the color of the redox liquid indicator can be readily observed.

In another embodiment of the apparatus, the ampoule is covered by an absorbent pad or layer, such as a non-woven layer of polyester fibers, which is then surrounded by a gas permeable bag, such as one woven or knitted of synthetic material. Upon curshing the ampoule the liquid therein is released and absorbed on the absorbent layer. The presence of oxygen is determined by the observed color of the absorbent layer. The outer bag serves to hold the absorbent layer together and prevents escape of the ampoule fragments after it is crushed.

The invention will be described further in conjunction with the attached drawings, in which.

Figure 1:
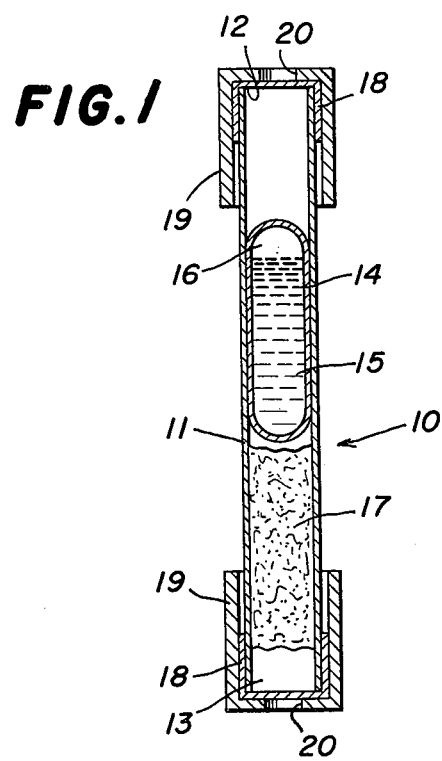
FIG. 1 is a longitudinal axial sectional view of a color indicator apparatus provided by the invention.

The color indicator apparatus 10 shown in FIG. 1 has an elongated flexible transparent tube 11 which is open at its ends 12 and 13. Tube 11 can be made of any suitable material although a flexible polymeric material such as polypropylene is particularly suitable for the tube. Ampoule 14 is snugly positioned within tube 11. The ampoule 14 may be made of any suitable material but desirably is made of relatively thin glass so that it can be easily opened by fracturing the ampoule walls by applying finger pressure against the adjacent surface of tube 11.

The ampoule 14 contains a liquid redox color indicator 15 which occupies most if not all of the space in the ampoule. The ampoule 14 shown in FIG. 1 may contain about 0.3 to 0.6 ml. of liquid and has a top space 16 filled with an inert gas such as nitrogen.

A fibrous liquid absorbent plug 17 is snugly positioned in tube 11 below ampoule 14. The fibrous plug 17 is made of a material which is nonreactive with the redox liquid such as polyester fibers or some other such liquid absorbent material.

It is considered advisable to cover each end of tube 11 with a bacteriological filter 18 through which microorganisms will not pass. In this way, any organisms in tube 11 are prevented from escaping to contaminate the surrounding environment. Each filter 18 is gas permeable but is also, desirably, one which is impermeable to liquid at low pressure, particularly water. The filter 18 at each end of the tube is held in place by a cap 19 having a hole 20 in the top portion.

The redox color indicator liquid 15 may be selected from any sutable material which will change color when the atmosphere around it changes from one which is oxygen-free to one where there is a significant or substantial amount of oxygen in the atmosphere. Thus, the indicator may have one color in the presence of oxygen and a different color in an atmosphere which is deficient of oxygen. Also, the indicator may be colorless when the oxygen content is very low and develop a color when oxygen is present, or the indicator may be colorless when oxygen is present and develop a color when the oxygen content is very low in the surrounding atmosphere.

A particularly useful redox color indicator is resazurin in water. This redox indicator is colorless in an atmosphere devoid of oxygen but in an oxygen-containing atmosphere it has a pink color. When this indicator is used it is advisable to include a small amount of cysteine hydrochloride with it since this ingredient facilitates color change. Another specific redox color indicator which may be used is methylene blue. This indicator is colorless in the absence of oxygen but in oxygen, such as in the presence of air, it has a blue color. It is furthermore desirable that the redox color indicator used be one which is color reversible so that any change from an oxygen-containing atmosphere to an atmosphere devoid of oxygen, or from an atmosphere devoid of oxygen to one containing oxygen, will be indicated by the color change.

The preferred redox color indicator for use in the apparatus is aqueous resazurin containing cysteine. A 0.001% solution of resazurin in water is specifically useful.

The described redox color indicator apparatus can be used with a number of different prior art devices for determining whether an anaerobic condition exists in a container used for storing or transporting an anaerobic bacteria culture. It may be used, for example, in conjunction with the system disclosed in Brewer U.S. Pat. No. 3,246,959. It may also be employed in conjunction with a conventional candle-jar widely employed in microbiology to determine whether an oxygen-free atmosphere has been produced.

Figure 2:
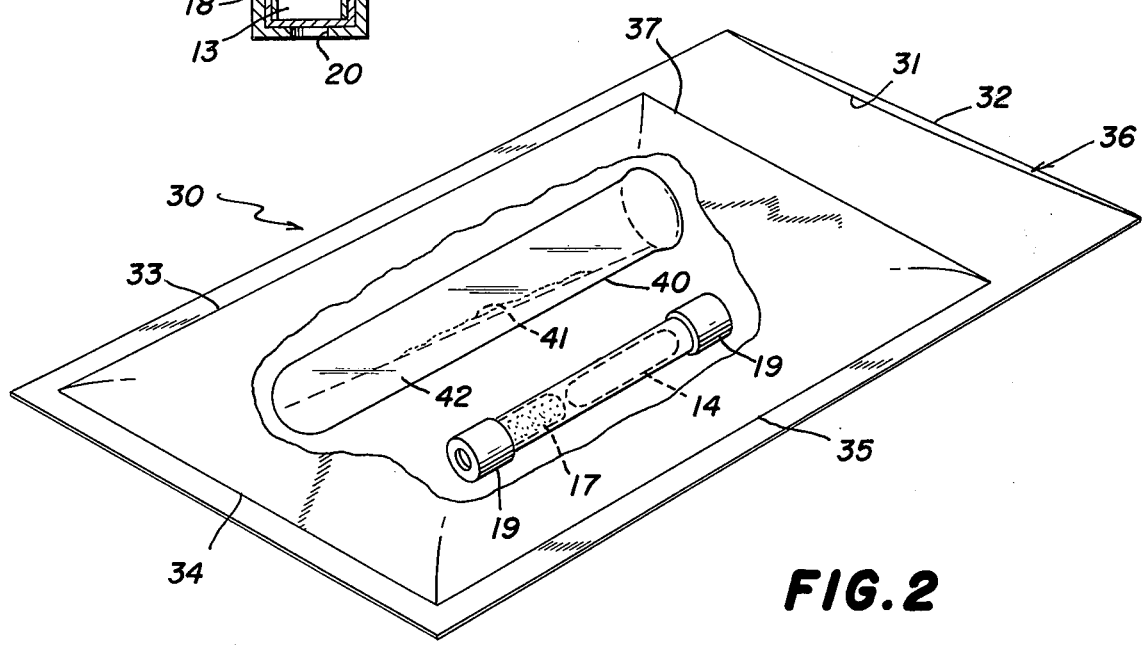
FIG. 2 is a perspective view of a representative package, for storing and transporting a bacteria culture, containing the color indicator apparatus of FIG. 1.

A further representative system in which the color indicator may be employed in shown in FIG. 2. The culture transport package shown in FIG. 2 has a bag 30 made of two layers 31 and 32 of clear polymeric film or sheet material of very low gas permeability heat sealed together about edges 33, 34 and 35, leaving mouth 36 open. Culture tube 40 having an anaerobic culture 41 on agar slant 42 is positioned in the bag 30. Color indicator apparatus 10 is also positioned in bag 30. With bag 30 positioned vertically, and with the color indicator apparatus 10 also vertically located, the tube 11 is squeezed adjacent ampoule 14 to crush the ampoule and release the color indicator liquid 15 permitting it to flow downwardly to be absorbed on fibrous plug 17. Since bag 30 contains air the plug 17 will quickly develop a pink color when the indicator liquid is resazurin. The interior space of bag 30 is then flushed free of air by means of a gas line which supplies nitrogen or some other gas to the interior of bag 30. Gas continuously flows through tube 11 because of holes 20 in each of the caps 19 and because of the elimination of the obstructing ampoule by crushing it to release the liquid redox indicator. As th air containing oxygen is flushed from bag 30 the pink color of fibrous plug 17 changes in color from pink to faint pink and finally to the natural color of the plug, which usually will be white. The composition of the gas in tube 11 quickly corresponds with that outside of the tube. When the pink color of plug 17 entirely disappears the atmosphere in bag 30 is indicated to be deficient in oxygen and thus suitable for storage and transport of the anaerobic culture. The mouth 36 of bag 30 may then be closed against gas flow by any suitable means, such as by a heat seal 37 extending completely across the width of the bag. If there is any subsequent oxygen penetration into bag 30 the indicator plug 17 will return to a pink color. It is also feasible to remove the oxygen from bag 30 by chemical means employing aqueous potassium hydroxide and aqueous pyrogallic acid as is disclosed in Anandam U.S. Pat. No. 3,616,263.

The redox color indicator 10 is readily sterilized by conventional means.

Figure 3:
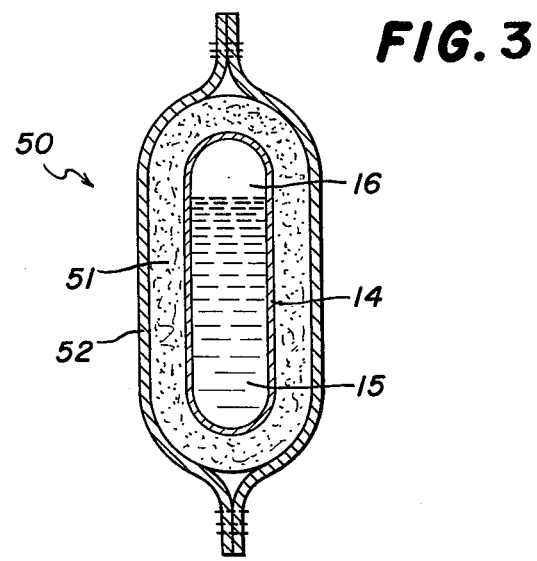
FIG. 3 is a longitudinal axial sectional view of a second color indicator apparatus embodiment.

The color indicator apparatus 50 shown in FIG. 3 has ampoule 14 surrounded by an absorbent layer 51 or pad of nonwoven material, such as polyester fibers. A loosely woven or knitted gas permeable fabric covers the absorbent layer. The fabric may be in the form of a bag 52, which may be made of a tube closed at both ends. The bag 52 covers the layer 51 to hold it in place and prevent escape of ampoule fragments when it is crushed. The described color indicator apparatus 50 is used in the same way as apparatus 10 and is interchangeable therewith in most applications. By pressing firmly on bag 52 the ampoule 14 is crushed thereby releasing the color indicating liquid 15 which is absorbed on layer 51. The color of layer 51 is observed through bag 52 thereby indicating whether oxygen is present.

The foregoing detailed description has been given for clearness of understanding only, and no unnecessary limitations should be understood therefrom, as modifications will be obvious to those skilled in the art.

What is claimed is:

1. A color indicator apparatus for determining the presence of oxygen which comprises:
    a flexible polymeric tube open at both ends,
    an ampoule in and in contact with the tube, said ampoule containing a redox color indicator liquid,
    an absorbent material, for the liquid in the ampoule, in the tube, and
    a gas permeable, liquid impervious, bacteriological filter at each end of the tube.

2. A color indicator apparatus for determining the presence of oxygen which comprises:
    a flexible polymeric tube open at both ends,
    an ampoule in and in contact with the tube, said ampoule containing a redox color indicator liquid,
    an absorbent material, for the liquid in the ampoule, in the tube,
    a gas permeable, liquid impervious bacteriological filter at each end of the tube, and
    a cap, having a hole therein which permits passage of gas, on the end of each tube to hold the filters in place and the absorbent material and ampoule in the tube.

* * * * *